US008884048B2

(12) United States Patent
De Munck et al.

(10) Patent No.: US 8,884,048 B2
(45) Date of Patent: Nov. 11, 2014

(54) PROCESS FOR PRODUCING ESTERS

(75) Inventors: Nicolaas Anthony De Munck, Barendrecht (NL); Brady Compton, Baton Rouge, LA (US); John Lyford, IV, Baton Rouge, LA (US); Aad Gerrit Oskam, Rozenburg ZH (NL)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 12/527,020

(22) PCT Filed: Mar. 7, 2008

(86) PCT No.: PCT/EP2008/001837
§ 371 (c)(1),
(2), (4) Date: Jan. 20, 2010

(87) PCT Pub. No.: WO2008/110305
PCT Pub. Date: Sep. 18, 2008

(65) Prior Publication Data
US 2010/0130767 A1     May 27, 2010

Related U.S. Application Data

(60) Provisional application No. 60/906,732, filed on Mar. 13, 2007.

(51) Int. Cl.
*C07C 67/08* (2006.01)
*C07C 67/14* (2006.01)
*C07C 67/303* (2006.01)

(52) U.S. Cl.
CPC .............. *C07C 67/08* (2013.01); *C07C 67/303* (2013.01); *C07C 2101/14* (2013.01)
USPC ........................................................ 560/99

(58) Field of Classification Search
CPC ........ C07C 67/08; C07C 69/80; C07C 69/76; C07C 305/10
See application file for complete search history.

(56) References Cited

U.S. PATENT DOCUMENTS

| | | | |
|---|---|---|---|
| 2,834,801 A | 5/1958 | Aldridge et al. | |
| 5,324,853 A | 6/1994 | Jones et al. | |
| 5,880,310 A | 3/1999 | Ageishi et al. | |
| 6,093,845 A * | 7/2000 | van Acker et al. | 560/239 |
| 6,235,924 B1 | 5/2001 | McConnell et al. | |
| 6,284,917 B1 * | 9/2001 | Brunner et al. | 560/127 |
| 6,310,235 B1 | 10/2001 | Gick | |
| 6,355,817 B1 | 3/2002 | Woods et al. | |
| 6,355,872 B2 | 3/2002 | Park et al. | |
| 6,888,021 B2 | 5/2005 | Brunner et al. | |
| 6,916,950 B2 | 7/2005 | Gubisch et al. | |

FOREIGN PATENT DOCUMENTS

| | | |
|---|---|---|
| DE | 2823165 | 11/1979 |
| DE | 10043545 | 3/2002 |
| DE | 10149350 | 4/2003 |
| EP | 1 300 388 | 4/2003 |
| JP | 11189569 | 7/1999 |
| WO | WO 99/32427 | 7/1999 |
| WO | WO 2005/002182 | 1/2005 |
| WO | WO 2005/021482 | 3/2005 |

OTHER PUBLICATIONS

Dr. H. Suter: "Continuous Production of Phthalic Esters From Phthalic Anydride and High-boiling Alcohols", Chemie-Ing.-Techn., vol. 41, pp. 971-974, (1969).
Brink et al.: Technical Mathematics for Chemical Industry Jobs, $3^{rd}$ Edition, pp. 138; Verlag Europa-Lehrmittel Haan-Gruiten, (2001).
Ullmann's Encyclopedia of Industrial Chemistry; $6^{th}$ Edition, vol. 26, pp. 512-515; Wiley-VCH, Weinheim, (2003).
Documents regarding BASF and Evonik Oppositions, 19 pages, 2011.

* cited by examiner

*Primary Examiner* — Fereydoun G Sajjadi
*Assistant Examiner* — Jennifer C Sawyer
(74) *Attorney, Agent, or Firm* — Leandro Arechederra, III; Luke A. Parsons

(57) ABSTRACT

A process for producing esters comprises esterifying an acid or anhydride with an excess of an alcohol to produce a crude ester, recovering excess alcohol from the crude ester and recycling recovered excess alcohol to the esterification reaction together with fresh alcohol. The process is improved by controlling the ratio of the amount of recycled alcohol and the amount of fresh alcohol in dependence on the level of impurities in the recycle alcohol. Further improvements come from feed forwarding fresh alcohol analysis results and from preheating the alcohol before loading into the reactor. Preferably, ester product quality is improved by stripping the alcohol for oxygen removal prior to esterification.

8 Claims, 1 Drawing Sheet

PROCESS FOR PRODUCING ESTERS

CROSS REFERENCE TO RELATED APPLICATIONS

This application is a 371 National Stage Application of International Application No. PCT/EP2008/001837, filed Mar. 7, 2008, which claims the benefit of Provisional Application No. 60/906,732, filed Mar. 13, 2007, the disclosures of which are herein incorporated by reference in their entireties.

FIELD OF THE INVENTION

The present invention relates to improvements in or relating to the production of esters, particularly but not exclusively plasticiser esters.

BACKGROUND OF THE INVENTION

Esters are produced by the reaction of an alcohol with a carboxylic acid or a carboxylic acid anhydride. In many instances, one or more of the starting materials may be a mixture. The carboxylic acid may be a mono or a polycarboxylic acid or the anhydride thereof. Plasticiser esters are generally produced from polycarboxylic acids or the anhydrides thereof and in particular from phthalic anhydride, cyclohexanoic dicarboxylic acid or its anhydride, adipic acid or anhydride or trimellitic acid or anhydride. Esters of benzoic acid, such as isononyl benzoate or isodecyl benzoate, are examples of plasticiser mono-esters. Esters may be produced from any alcohol, but plasticiser esters are generally produced from $C_4$ to $C_{13}$ alcohols and in particular $C_6$ to $C_{13}$ alcohols more typically $C_8$ to $C_{10}$ alcohols.

The production of esters and in particular plasticiser esters is described in U.S. Pat. Nos. 5,324,853; 5,880,310; 6,310,235 and 6,355,817. All of these patents disclose that the esterification reaction is reversible and that excess alcohol is preferably used in the esterification reaction to drive the reaction to completion. U.S. Pat. Nos. 5,324,853 and 6,355,817 suggest that the excess alcohol be collected after the esterification reaction and recycled. The present invention is particularly concerned with optimising the recycle of alcohol to the esterification reaction.

It is known from U.S. Pat. No. 5,880,310 that oxygen should be removed from alcohols used in the production of plasticiser esters. The oxygen is removed in order to improve the colour of the final ester. It is also known that esterification reaction cycle time can be reduced if the alcohol is preheated before it is fed to the esterification reactor.

No consideration has been given however to the optimisation of the recycle of alcohol. In reaction systems in which alcohol is recycled to the esterification reaction the recycle alcohol is mixed with fresh alcohol in proportions such that the appropriate level of excess alcohol is fed to the esterification reaction. However, the fresh alcohol feed is generally not 100% pure alcohol, but contains some residues from the alcohol manufacture such as olefins, paraffins and olefin oligomers. The fresh alcohol may also include for example traces of aldehydes, formate esters, di-alkyl esters and ethers, cyclic ethers, and peroxide inhibitors from the olefin feedstock used in the production of the alcohol. The alcohol manufacture is typically accomplished by either olefin oligomerisation followed by hydroformylation followed by hydrogenation, or olefin hydroformylation followed by aldol condensation followed by hydrogenation. Whichever process is used and whatever purification techniques are used, the resulting alcohol will typically contain some impurities. These impurities will generally not participate in the esterification reaction and accordingly will pass through the esterification reaction and remain in the recovered excess alcohol, and/or pass through with the crude ester product.

After esterification the crude ester will contain contaminants and requires purification. These contaminants may belong to the family of acidic residues, unreacted alcohol, catalyst residues, water and the contaminants that were already present in the alcohol feed, most of these being so-called monomeric components that are eluted in the so-called "light ends" region of the plasticiser Gas Chromatogram or GC-spectrum.

The crude esters may also contain byproducts, such as alcohol (di-alkyl) ethers, benzoate esters, mono-esters from dibasic acids, alcohol oxo acid esters, hemiacetals and vinyl ethers (these are so-called dimeric components, because they originate from a combination reaction of two molecules of the starting materials, and are often collectively called "ethers" or "intermediates" due to their elution in the plasticiser Gas Chromatogram or GC-spectrum between the monomeric light ends and the "trimeric" target product diesters). In the production of triesters, such as trimellitates, also so-called "trimeric" compounds because they combine three molecules of starting material, such materials as e.g. acetals or diesters, may be considered "intermediate" impurities. Many of these dimeric or other intermediate materials, including acetals, may become hydrolysed, in particular during later stages in the esterification process, to form odour formers such as aldehydes and/or other light ends, which often add to the so-called monomeric component part of the contaminants. Trimeric components may also add to the dimeric contaminants when they break apart, such as by hydrolysis. Any of such impurity component that is sufficiently volatile and is formed before the last recovery step of excess alcohol, may end up as a contaminant of the recycle alcohol. Other impurities may be generated as byproducts in the esterification reaction and remain in the recovered excess alcohol. These can include mono-esters in the case of di-ester production, di-esters in the case of tri-ester production, phthalide in the case of phthalate production, alcohol benzoates if benzoic acid is present as an impurity in the acid or acid anhydride, maleates if maleic acid or anhydride is present, and phthalic acid in case where phthalic anhydride is used. Also these components may show up as impurities in the recycle alcohol.

In the steps taken for removal of the excess alcohol from the crude ester product mixture, some of the product ester may also end up in the recycle alcohol. Upon recycle of the recovered excess alcohol, this product ester is not lost. This amount of ester however dilutes the recycle alcohol. These product ester compounds in the recycle alcohol may therefore also be considered as impurities.

The impurity level in the recovered excess alcohol will be considerably higher than in the fresh alcohol. Accordingly, when this recovered excess alcohol is recycled to the esterification reaction, this will cause a build up of impurities in the fresh alcohol/recycle alcohol mixture which is fed to the esterification reaction, particularly in reactions involving repeated recycles. Accordingly, a series of recycles can result in a level of impurities as high as 20 to 30% by weight in the excess alcohol recovered and recycled to the esterification reaction. This, in turn, leads to a distortion in the projected alcohol to acid molar ratio in the esterification reaction, leading to a lower, if any, excess alcohol level and hence a less complete reaction or the need for a longer reaction time. Because typically a target conversion needs to be reached in order to achieve target production economics, this results in a batch time that is unpredictable and typically understated.

Therefore samples need to be taken and analysed to assure the target degree of reaction, often expressed as a target conversion, is reached. The sampling and analysis time is therefore added to the batch time, which reduces productivity.

The present invention addresses these problems.

SUMMARY OF THE INVENTION

The present invention therefore provides a process for producing an ester which comprises
(i) esterifying an acid or anhydride with an excess of an alcohol to produce a crude ester,
(ii) recovering excess alcohol from the crude ester formed by the esterification, and
(iii) recycling recovered excess alcohol to the esterification reaction together with fresh alcohol,
characterised by controlling the ratio of the amount of recycled alcohol and the amount of fresh alcohol in dependence on the level of impurities in the recycle alcohol.

The ratio of recycled alcohol to fresh alcohol is preferably adjusted to control the true molar excess of the alcohol in the esterification reaction, in particular at the start of the esterification reaction. This control brings the advantage that the kinetics of the esterification reaction are under tighter control, and enhances the predictability of the reaction time required to reach the target conversion. It also reduces the need for analytical monitoring.

In a further embodiment the amount of recycle alcohol is adjusted to take into account the monomeric impurity components, i.e. that typically elute in the "light ends" region of the recycle alcohol GC-spectrum, before the alcohol component. In a preferred embodiment, the amount of recycle alcohol is adjusted to take into account also the product ester impurities in the recycle alcohol. In a yet more preferred embodiment, in particular when esters of a polybasic acid or anhydride are produced, the amounts of alcohol are adjusted to also take into account the intermediate impurity components, i.e. those that elute in the ester GC-spectrum between the monomeric light ends and the target product esters, and which show up in the recycle alcohol GC spectrum following the alcohol components but before the product ester components. In the production of diesters, these intermediate impurity components comprise the so-called dimeric components. In the production of triesters, these may also comprise trimeric components.

DETAILED DESCRIPTION OF THE INVENTION

We have found that a convenient way to take into account the impurities in the recycle alcohol is to analyse the fresh alcohol feed and determine the level of impurities in the fresh alcohol feed. This may then be used to predict the level of impurities in the recycle alcohol, primarily the amount of monomeric impurities to be expected, which may be accomplished before the excess alcohol is recovered and isolated, and allow the appropriate adjustment to be made to the next batch within acceptable accuracy limits. In this way the need to wait for an actual analysis of the composition of the recycle alcohol is avoided. This predicted level of impurities may periodically be checked against an actual analysis result of the recycle alcohol, and, if necessary, the controls may then be adjusted to keep the amount of real excess alcohol in the reactor closer to its target level. This procedure is particularly advantageous when the feed alcohol purity is variable and the level of impurities is less consistent, for instance when feed alcohols from different supply sources are being used sequentially.

In a typical esterification process the fresh alcohol feed is generally above 99% pure, typically above 99.5%. The recycle alcohol typically has a purity in the range 70 to 95% and accordingly adjustment of the alcohol feed recipe, in dependence on the composition of the recycle alcohol feed according to the present invention, allows high reactor productivity to be retained due to the optimisation of the alcohol to acid or anhydride ratio in the esterification reaction. The present invention also allows a more reliable prediction of the batch time required to reach a target conversion without the need to wait for the results of an analysis of the recycle alcohol. The esterification batch can therefore be terminated on a prescheduled sequence, while the analytical result is used later on to verify the accuracy of the batch time prediction. This allows a significant gain in reactor productivity. In addition, when the reaction kinetics are known with sufficient accuracy, in particular with a single isomer alcohol starting material, this allows the expected time to reach the target conversion to be calculated accurately from an analytical result of a sample taken several minutes before the expected batch termination time and avoids the waiting time for the analytical result as previously required. If the sample is taken at least 2 minutes, preferably at least 3 or 4 minutes, more preferably about 5 minutes, and preferably not more than 10 minutes before the batch termination time, sufficient time is available to generate the analytical result and to calculate the expected batch termination time more accurately. This permits termination of the batch at a more appropriate time, such that the target conversion is reached more accurately while optimal reactor productivity is approached much more closely. Taking the sample not more than 15 minutes before the expected batch time is preferred, because then the further progress of the reaction is easier to predict than when the sample is taken earlier. These times are very suitable for phthalate esters. However, with slower reacting raw materials the sample may be taken much earlier, up to 1 hour, 1.5 hr or more before the expected batch termination time, still allowing an accurate prediction of the further progress of the reaction until the target conversion is expected to be reached.

It is known that the higher the initial level of the excess reagent in the esterification reaction, which in many cases is the alcohol, the higher the rate of the esterification reaction and hence the lower the batch cycle time. However, a higher level of the excess reagent reduces the productivity of the reactor batch and of the downstream purification equipment, due to the dilution effect and the need to handle higher volumes of material. In addition, the greater volume of material requires a greater amount of energy to remove and recover the excess reagent. In the production of phthalate di-esters, we prefer to operate with a true (excluding impurities) molar stoichiometric excess of alcohol, relative to phthalic anhydride, from 22 to 32%, more preferably from 24 to 29%, even more preferably from 25 to 27%, and most preferably at 26±0.5% molar, i.e. 2.52 moles of alcohol per mole of phthalic anhydride. Tight control of this true molar excess enhances the predictability of the batch time to reach the target conversion and reduces the need for analytical monitoring. Respecting these upper limits on alcohol excess is important in particular for esterification equipment that is pushed in throughput towards its maximum heat supply capabilities, which is very often the case.

In the production of phthalate esters, the preferred molar excess ratios are dependent on the grade of phthalate di-ester being produced. For di-isoheptyl phthalate (DIHP), we prefer to work with an excess of 30%, for di-isononyl phthalate (DINP) we prefer to work with 28% excess, and for di-isodecyl phthalate (DIDP) and for di-isoundecyl phthalate (DIUP) we prefer to use 26.5% excess. We prefer not to deviate more than 1.5% upwards or downwards from this preferred level, more preferably not more than 1.0% and even more preferably not more than 0.5%, because this ensures fewer swings and smaller deviations from optimal in the pressure-temperature profile once the reaction temperature has reached the minimum desired esterification reaction temperature of 210° C. This is the part of the reaction pressure and temperature profile where reaction temperature should preferably be as close as possible to the 220° C. upper limit for titanium catalyst activity and stability, while the control setpoint on reactor pressure is pushed down to enable rapid removal of vapours whilst maintaining the temperature, which is dependent on the heat input capabilities. If the reaction temperature declines away from its target, the pressure setpoint reduction slope may be temporarily overridden to allow the temperature to regain its previous level, after which the pressure setpoint is again allowed to drop. The temperature decline that triggers the control override is product grade dependent, but is typically no more than 2 degrees C., preferably no more than 1 degree C. The profile of the pressure setpoint is also dependent on the amount of catalyst that is dosed into the reactor. In a high catalyst dosing scenario, the reaction goes faster and the pressure can be reduced faster. In a lower catalyst dosing scenario, typically when plant throughput is below maximum, a less aggressive pressure setpoint reduction profile is used.

The ester molecules produced using the process of the invention may comprise aromatic rings, such as alkyl benzoates, di-alkyl phthalates or tri-alkyl trimellitates. The aromatic rings in these ester molecules may be hydrogenated to produce the corresponding cyclohexane equivalents, such as mono-alkyl, di-alkyl or tri-alkyl cyclohexanoates. In particular, DINP may be further hydrogenated to form di-isononyl di-cyclohexanoate (DINDCH). The process of the invention may therefore be for the production of a phthalate di-ester, in particular DINP, and further comprise the hydrogenation of the phthalate di-ester to the corresponding di-cyclohexanoate, in particular DINDCH. Suitable hydrogenation processes are disclosed in EP 1042273, US 2004/0260113 or WO 2004/046078.

Esterification reagents may contain a certain amount of oxygen, in particular when they have been stored and/or shipped in containers that are emptied using compressed air, or that are allowed to "breathe", i.e. are in contact with atmosphere such that any temperature swings, caused e.g. by day-night or weather differences, cause ingress of atmospheric oxygen into the container and hence into the esterification reagent. Whilst it is known that oxygen should be removed from fresh alcohol feeds to esterification reactions, we have found that oxygen removal is particularly important in systems employing recycle alcohol that contains impurities. We do not know the mechanism but this suggests that, at the high levels of impurities in the recycle alcohol, there is some interaction between oxygen and the impurities, and this may cause colour formation. Removal of oxygen, in particular from fresh alcohol feed that has been transported from other production sites, allows good colour ester to be produced.

Further exclusion of oxygen may be achieved by providing a nitrogen blanket above the liquid level in alcohol feed tankage. We have found that, in the production of phthalate esters, the phthalic anhydride (PAN) feed to the esterification reaction, particularly when it is loaded as flakes, may also bring in oxygen. We therefore prefer to provide intensive nitrogen purging during the loading of PAN flakes into the reactor, thereby avoiding colour formation in the phthalate ester product.

Accordingly it is preferred that oxygen be removed from the fresh alcohol before it contacts the recycle alcohol. In a preferred process, fresh alcohol is first deoxygenated, then mixed with the recycle alcohol in the appropriate ratio, and the mixture fed to the esterification reaction vessel. We have found that stripping with nitrogen is a convenient method for the removal of oxygen, but steam and/or any other inert gas may also be suitable. This can be done by bubbling nitrogen through the alcohol in the esterification reactor, or more preferably in a separate vessel, via the bottom valve of the container, or via a specially designed and dedicated nitrogen gas sparger provided inside the container below the liquid level, preferably as low as possible.

In a further embodiment, both the fresh alcohol and the recycle alcohol, or their mixture, are preheated before being fed to the esterification reaction vessel. We prefer that both alcohol streams are heated to a temperature in the range 100 to 160° C. This preferred preheating temperature is grade dependent, because of the change in boiling point. Excessive preheating is to be avoided in order to keep alcohol vapor losses from the preheating step within acceptable limits. For DIHP we prefer to preheat the isoheptyl alcohol to 100-115° C., for DINP and DIDP we prefer to preheat the isononyl or the isodecyl alcohol to 130-150° C., and for DIUP or di-isotridecyl phthalate (DTDP) we prefer to preheat the isoundecyl or isotridecyl alcohol to 130-155 or even up to 160° C. We also prefer that the fresh alcohol be preheated before oxygen removal, since we have found that preheating improves the oxygen removal, particularly if the oxygen removal is accomplished by the preferred technique of nitrogen stripping. We have found that nitrogen stripping of preheated fresh alcohol brings a product colour improvement of 5-10 on the Pt/Co scale in the production of di-isodecyl-phthalate, when compared to nitrogen bubbling before the fresh alcohol is preheated. We have also found that it is important to perform the nitrogen stripping on the alcohol reactant in absence of the acid or anhydride component. The preheating may advantageously be provided by cooling the crude ester produced in the esterification reaction, preferably by heat exchange prior to the neutralisation step. This at the same time cools the crude ester for its next treatment, which is typically required. This heat exchange between crude ester and alcohol is more easy to accomplish if the finishing process, i.e. the treatment from neutralisation onwards, is operated continuously. It is also easier if the alcohol preheating can be performed in one or more vessels separate from the reactor, so that it can be performed at a convenient moment. It is also easier to operate if several batch esterification reactors operate in parallel but in a staggered sequence mode, so that heat from a reactor batch being terminated is available for another reactor batch that is starting.

Figure 1:
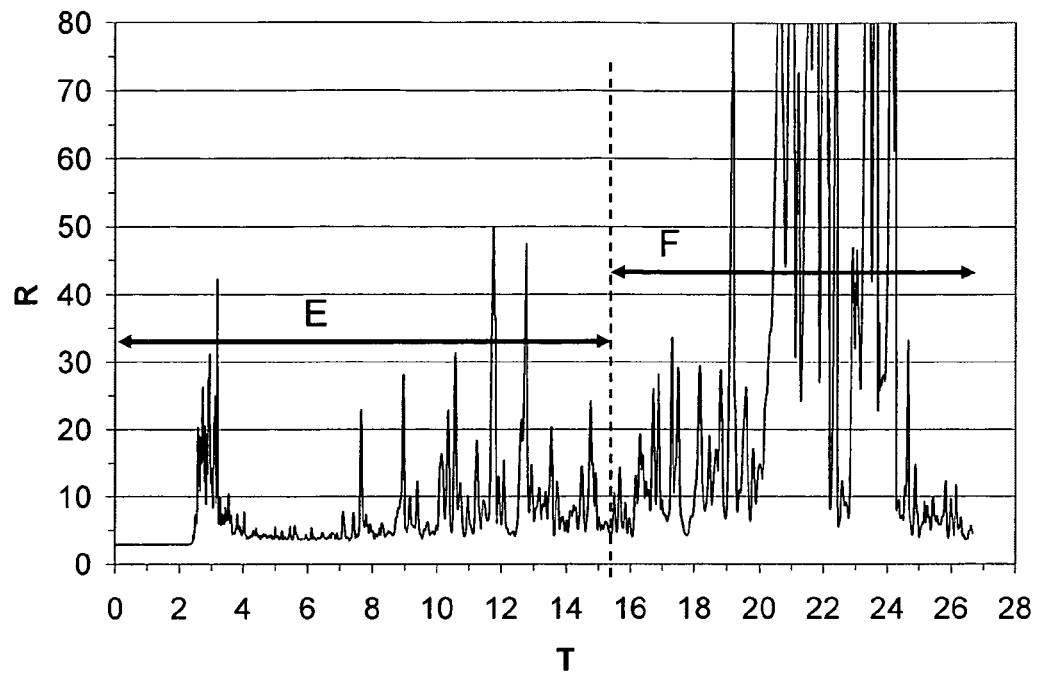
FIG. 1 shows a GC-spectrum of a typical recycle isodecyl alcohol in the production of di-isodecyl-phthalate ester (DIDP), using a method that focuses on determining monomeric impurities in the alcohol.

A representative sample is injected into the capillary of a gas chromatograph using a split/splitless injector. A part of the sample is brought into a fused silica column coated with a medium polar stationary phase, such as CP Wax 52. The a-polar hydrocarbons (olefins/paraffins) and other lighter components are separated from the alcohol isomers, and the heavier, so-called "intermediate" impurities may also elute, separately and after the alcohol components. Retention time windows are defined to calculate the concentrations of alcohols, and of components that are lighter than the alcohols. The windows are different for each individual alcohol grade, which may typically only primarily differ in average carbon number. The method is also suitable to determine the carbon number distribution of the alcohols, by determining retention time windows for the respective alcohol carbon numbers. We then prefer to use the retention times of the normal alcohols as the window delimiters, under the assumption that the n-alcohols are the longest retained isomers within one carbon number group. This method may possibly be used, but is less suitable, to determine the heavier impurity components as discussed before, for which we prefer to use a different method. The retention time windows can be readily defined based on comparisons of GC-spectra of the recycle alcohol with this of the fresh alcohol, and these windows can readily be defined for each of the starting alcohols in case different esters are produced from different starting alcohols. Gas Chromatography in combination with Mass Spectroscopy (GC-MS) may provide further guidance in determining the identity of certain GC-peaks, and thus in setting retention time windows for non-alcohol components and for the individual carbon numbers. Calculations of the concentrations of the individual groups may be carried out using an automated spreadsheet calculation and by a reporting program that may be started automatically by the post-run program of the GC method.

The following apparatus may be used:

| | |
|---|---|
| Chromatograph | Hewlett Packard 5890 series II equipped with an auto-sampler, split-splitless injector and a flame ionisation detector (FID) or equivalent. |
| Column | Chrompack, CP Wax 52, fused silica, with a length of 50 m, 0.25 mm internal diameter (ID), and a film thickness (DF) of 0.2 µm. |
| Syringe | 10 µL for HP auto-sampler or equivalent. |
| Integrator | Hewlett Packard HP-Chemstation or equivalent. |

The following gases and gas rates may be used:

| | |
|---|---|
| Carrier gas | Hydrogen, 2 ml/min |
| Split flow | 150 ml/minute; for the recycle alcohol we prefer to use 180 ml/minute |
| Detector gas | Hydrogen, 30-40 ml/min |
| | Air, 300-400 ml/min; for the recycle alcohol we prefer 400-500 ml/min |
| | Nitrogen, +/−30 ml/min (Auxilliary gas) |

The following conditions may be employed in the apparatus:

Auto Sampler

| | |
|---|---|
| Sample washes = | 9 |
| Sample pumps = | 9 |
| Injection volume = | 1 µL; for the recycle alcohol we prefer only 0.5 µL |
| Viscosity Delay = | 4 sec, for the recycle alcohol preferably 3 seconds |

Injector

| | |
|---|---|
| Injector temperature = | 250° C. |

Detector

| | |
|---|---|
| Detector temperature = | 300° C. |

Oven—Temperature Programming

| | |
|---|---|
| Initial oven temperature = | 80° C. |
| Initial time = | 5 minutes |
| Temperature rate 1 = | 2 degrees Celsius/minute |
| Final temperature 1 = | 140° C. |
| Final time 1 = | 5 minutes, 10 minutes for fresh alcohols above C10 |

For the recycle alcohol analysis we prefer to extend the temperature programme as follows:

| | |
|---|---|
| Temperature rate 2 = | 10 degrees Celsius/minute |
| Final temperature 2 = | 250° C. |
| Final time 2 = | 9 minutes |
| Total analysis time = | 40, 45 or 60 minutes depending on alcohol |

The information on the temperature programming means that the column in the oven is brought up to an initial temperature of 80° C. (and held there for about 2 minutes) before the sample is injected. After sample injection, the oven is kept at this 80° C. for 5 minutes after which the temperature is raised at a rate of 2 degrees Celsius/minute until the final temperature 1 of 140° C. is reached, where the oven is kept for another 5 minutes, or 10 minutes for a fresh alcohol above C10. At this time this analysis is considered finished. However, with a recycle alcohol, we prefer to continue the programme further in order to clean the column and prepare it for a new analysis. The column is then further heated to 250° C. at a rate of 10 degrees Celsius per minute, and held there for another 9 minutes. This removes the heavier material from the column which may otherwise impair the results of the subsequent analysis.

A standard production sample of fresh isononylalcohol is taken as a quality control sample. The calibration, and therefore the analytical result, is on a weight basis. Accordingly, the impurity level in the fresh and recycle alcohol feeds is determined by GC. Overall it calculates % hydrocarbons or "lights" and % alcohols, and optionally also % "intermediates". Non-alcohol components lighter than the alcohols are all considered part of the monomeric impurities. "Intermediates" are those components eluting after the alcohol components but before the product ester components.

A typical GC-spectrum, according to this first method, of a recycle isodecyl alcohol in the production of di-isodecylphthalate (DIDP) ester is shown in FIG. 1. The spectrum has a horizontal axis T indicating time in minutes (span shown is 28 minutes); and a vertical axis R indicating response in counts. The alcohol components form the majority of the composition and are found in the region indicated as F. The components eluting before the alcohols show up to the left, in the region indicated as E. Any dimeric components do not elute within the retention time window of 40 minutes with this method.

The above method is less suitable for determining the level of the heavier impurities in the recycle alcohol, such as the product ester and the intermediate impurities. If these are to be taken into account, e.g. in order to reach a higher level of accuracy, we prefer to analyse the recycle alcohol also using a second and different method, more similar to the method used to analyse the product ester and/or the light ends contents therein. This method typically uses an external standard for quantification, although an internal standard may also be used. An appropriate GC method using an internal standard is explained in detail in our copending application WO2005/021482.

The method is explained for the production of a di-phthalate ester of a plasticiser range alcohol. An external standard may have to be made for every product grade, by mixing a known amount of the product di-phthalate ester into a known amount of the corresponding fresh alcohol. We prefer to use a mixture of 2.00% wt of ester in 98.00% wt of alcohol as external standard.

The amount of product ester, and if desired also the amount of the intermediates, in a recycle alcohol sample may be measured by Gas Chromatography as follows:

The sample of recycle alcohol is injected on a non-polar GLC column, which separates the alcohol, optionally also the intermediates, and the di-phthalate ester using a temperature program. The area of the alcohol and the di-phthalate ester are compared to the area of the external standard and the concentration is calculated.

As apparatus we prefer to use a Gas Chromatograph with a wide bore capillary column. The preferred gaschromatograph may be equipped with an autosampler, has a split-splitless injection system and a flame ionisation detector (FID detector). Also a cool on column injector, such as manufactured by Gerstel Germany, may be used. The apparatus is further equipped with an integration and reporting system.

The column we prefer is a wide bore fused silica capillary column HP-1 (crosslinked Methyl Silicone Gum), with a length of 30 meter, an internal diameter of 0.53 mm and a 0.88 µm film thickness. Suitable types are HP No. 19095Z-023 or equivalent. An analytical balance is required to prepare the external standard.

The following GC conditions may be used:

| Auto sampler | |
|---|---|
| Sample washes | 9 |
| Sample pumps | 9 |
| Injection volume | 1 µL |
| Viscosity Delay | 4 seconds |
| Carriergas | Helium, 10 ml/min. |
| Split flow | 50 ml/min. |
| Detector gasses | Hydrogen, 30-40 ml/min. |
| | Air, 300-400 ml/min. |
| | Nitrogen, 20 ml/min. (supplementary gas) |
| Injector temp. | 300° C. |
| Detector temp. | 325° C. |

Oven Temperature Programming:

| | |
|---|---|
| Initial temp. | 50° C. |
| Initial time | 2 min. |
| Rate 1 | 50 degrees C./min. |
| Final temp. 1 | 150° C. |
| Final time 1 | 4 min. |
| Rate 2 | 10 degrees C./min. |
| Final temp 2 | 300° C. |
| Final time 2 | 12 min, 17 minutes for a recycle alcohol above C10 |

This means that the column in the oven is brought up to an initial temperature of 50° C. (and held there for about 2 minutes) before the sample is injected. After sample injection, the oven is kept at 50° C. for another 2 minutes after which the temperature is raised at a rate 1 of 50 degrees Celsius/minute, until the final temperature 1 of 150° C. is reached, where the oven is kept for another 4 minutes. Then the column is further heated at a rate of 10 degrees Celsius per minute until the final temperature 2 of 300° C. is reached, and held there for another 12 minutes or 17 minutes for an alcohol above C10.

Figure 2:
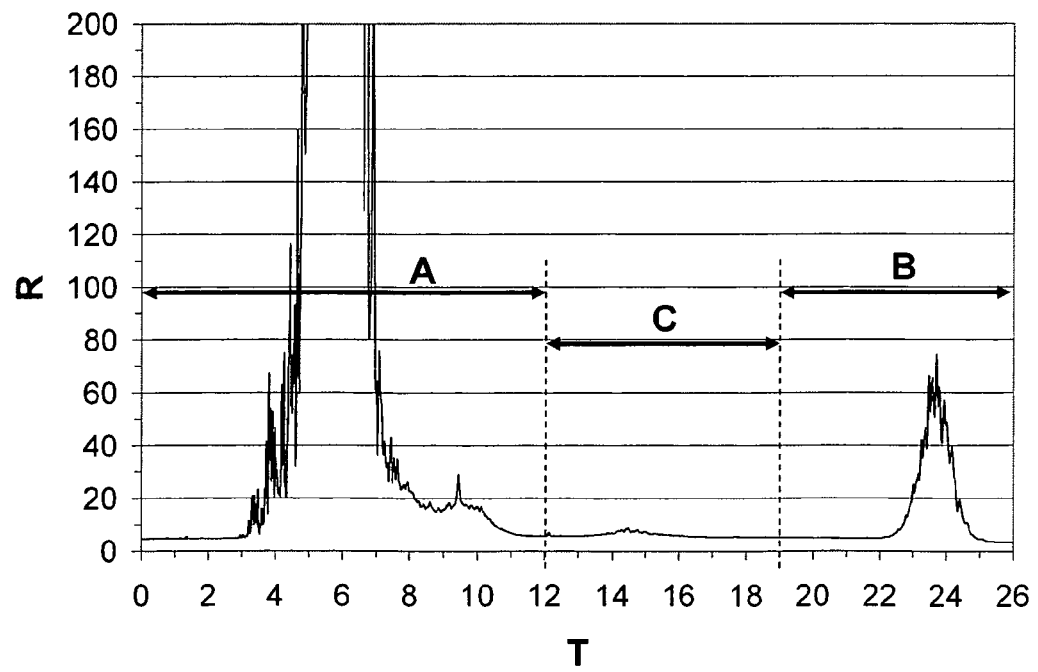
FIG. 2 shows a GC-spectrum of a typical recycle isodecyl alcohol using a method that focuses on determining product ester and intermediate impurities in the alcohol. The following method may be used to analyse for monomeric impurities in both fresh and recycle alcohol. The method is described for the fresh alcohol analysis. For the recycle alcohol analysis we prefer a method that slightly differs from the analysis of fresh alcohol, as indicated.

FIG. 2 shows a typical C10 recycle alcohol GC spectrum according to this second method, having a horizontal axis T indicating time in minutes (the span shown is 26 minutes); and a vertical axis R indicating response. The spectrum is blown up and shows, besides the alcohol components (in the window that is indicated as A), two more groups of peaks:

the plasticiser ester impurity peak itself (retention time above 19 minutes), in the window marked as B, and a group of components that are heavier than the alcohol, but not as heavy as the product ester (retention time above about 12 minutes but less than about 19 minutes. They are the group of intermediate impurities as they are defined in the composition of the recycle alcohol.

The windows for the different group of impurities, and if required also the temperature program of the GC apparatus, may be readily adapted to the kind of ester produced and the kind of starting materials used. This adaptation is considered to be within the capabilities of the normally skilled person.

The level of dimeric impurities, and trimeric impurities, if present, may be split off from the % "intermediates" by defining appropriate sub-windows, if needed by introducing (further) internal standards. The ester content of the recycle alcohol is typically in the range from 1 to 3% wt, more typically around 2% wt. Excursions up to 5% wt may occur, but are typically an indication of suboptimal conditions in one of the downstream steps for removal of excess alcohol from the product ester, or potentially a sign of a damaged demister or other related equipment item. The operations of the excess alcohol removal steps may be adjusted according to the alcohol grade that is processed, and these recycle alcohol analyses may provide guidance in determining the optimum conditions for those steps.

By the application of a mass balance model, it is possible to predict the buildup of the inerts in the recycle alcohol, and to predict the time of reaching the target of e.g. 75% wt alcohol content in the recycle alcohol. The mass balancing is based on the inerts content of the fresh alcohol as determined by GC, the actual production rate, the excess alcohol used for the esterification, the known alcohol holdup volume in the processing equipment and tankage, and known losses. From the mass balance model it is also possible to calculate the alcohol content in the recycle alcohol feed, allowing a more accurate calculation of the esterification reaction mixture that needs to be fed in order to achieve optimum reactor productivity. This allows for a more economical use of the esterification reactor and a reduced energy consumption, while maintaining product quality.

The decline in recycle alcohol purity can be calculated from the determination of the content of the impurities in the fresh alcohol, and the recipe may be adjusted to approach the targeted molar excess used for that particular alcohol grade. The recycle alcohol purity may then be periodically measured using one or both of the above methods, to test the calculated value and correct the recipe if needed.

Phthalic anhydride, and other esterification reagents that are typically solid at room temperature, are often transported, stored and/or introduced in a heated and molten form. This may cause potential problems in terms of solid formation in equipment and overhead vents, in evacuation ducts for equipment flushing and the like, creating risks of line or equipment plugging, or emission of solids to the atmosphere. These problems may be alleviated and/or eliminated by providing at appropriate places in the lines and equipment, sections where gas velocities are lower such that any solids formed easily settle out and may be collected. Alternatively, other conventional types of solid/fluid separation techniques may be employed, such as cyclones. These solids, often in the form of dust, may then be removed during the periods that that particular part of the line or equipment is not in use, and may be discarded or preferably recycled to the process.

The esters to which the present invention applies are typically plasticiser esters produced by the catalytic reaction of acids, generally polycarboxylic acids or anhydrides and alcohols. Typical esterification catalysts are titanium, zirconium and tin catalysts such as titanium, zirconium and tin alcoholates, carboxylates and chelates such as those described in U.S. Pat. No. 3,056,818 (Werber).

Selected acid catalysts may also be used in this esterification process. Some examples of acid catalysts are sulfuric acid, methyl sulfonic acid, benzene sulfonic acid, p-toluene sulfonic acid, naphthalene sulfonic acid, aluminum sulfate and aluminum powder.

Typical titanium alkoxides or alcoholates which can be used as catalysts include tetramethyl titanates, tetraethyl titanates, tetrapropyl titanates, tetra-isopropyl titanates, tetrabutyl titanates, tetra-isobutyl titanates, tetrapentyl titanates, tetrahexyl titanates, tetraheptyl titanates, tetra-octyl titanates including 2-ethyl-hexyl and iso-octyl, tetranonyl titanates including 2,4-dimethyl-heptyl and isononyl, tetradecyl titanates including 2-propyl-heptyl and isodecyl, tetradodecyl titanates, tetrahexadecyl titanates, tetra-octadecyl titanates, tetraphenyl titanates, and mixtures thereof. The alkoxy groups on the titanium atom can all be the same or they can be different, and their alkyl chains may be normal and/or branched, or mixtures thereof. The tin or zirconium counterparts of the above alcoholates can be substituted in whole or in part as catalysts.

A process that may be used for the production of the esters is described in U.S. Pat. No. 5,324,853 in which a process is disclosed for the catalytic esterification of acids or anhydrides with a mono-alcohol or a polyhydroxy compound. This process comprises the steps of adding either an acid or anhydride and a mono-alcohol or a polyhydroxy compound to a reaction vessel to form a reaction mixture, and heating the reaction mixture to a temperature in the range between about 150° C. to 280° C., preferably between about 180° C. to about 260° C. The pressure is maintained at a level sufficient to obtain boiling of the reaction mixture, thereby causing the esterification, and removing water as vapor while continuously mixing the reaction mixture in the reactor vessel, such that at least about 2.5 to about 20 volumes of reaction mixture are internally recirculated per minute (defining reactor turnover rate to be the volumes of reaction mixture internally recirculated per minute divided by the reaction mixture volume, continuously mixing the reaction mixture in the reactor vessel to achieve a reactor turnover rate of at least about 2.5 to about 20). We prefer that in the initial phase of the reaction the pressure is maintained at a superatmospheric level that allows vaporization and removal of the water of reaction but substantially prevents vaporization of the reactants. Such a process is described in our copending U.S. patent application U.S. Ser. No. 60/906,797 (applicant's reference PM2004-063). In this way the rate of conversion is enhanced and such that for plasticizer esters, limiting reagent conversions of greater than 99% are achieved and such that for polyol esters limiting reagent conversions of greater than 98% are achieved. It is still possible to heat the reagents at higher temperatures, such as up to 350° C., so long as the reagents remain stable.

Optionally and similar to what is explained in U.S. Pat. No. 5,324,853, the step of returning the reflux alcohol to the esterification reactor may use a reflux drier or non-reflux drier method for reducing the amount of water refluxed from the vapor taken overhead from the reaction vessel. The reflux drier method includes: passing vapor from the reaction vessel through a packed tower or column such that a portion of alcohol contained within the vapor is condensed and recycled to the reaction vessel, and wherein the remaining vapor is taken overhead; passing the remaining vapors through a condenser to an overhead collection drum which allows the alcohol and the water to separate into two liquid phases; separating the alcohol from the water; recycling the alcohol to the packed tower and contacting it with the vapor from the reaction vessel such that a portion or all of the water dissolved in the alcohol liquid is vaporised and taken overhead; optionally recycling the water from the overhead separator to the hydrolysis step; taking overhead the vapors from the collection drum for condensation of water contained therein; and optionally recycling the condensate from these vapors to the hydrolysis step. Such a reflux drier also brings the advantage of heat integration in the reactor overhead system. Sometimes a vapour bypass is provided over the reflux drier directly to the overhead condensor. The reflux drier may then be smaller because it does not need to handle the full vapour load coming from the reactor.

The limits on the amount of excess alcohol used are particularly important when the reactor overhead equipment is pushed towards its hydraulic limits, such as when the reflux drier operates close to its flooding limitation and/or the overhead condensor and separator operate close to their maximum capabilities. Under these circumstances, it is important to not push the alcohol excess above the respective upper limits. If this is done, free water may end up in the reflux to the reactor, or to the reflux drier, such as in the form of an emulsion of water in alcohol. This water may be partly recovered by the reflux drier, but this extra water recycle adds to the water load of the overhead system and aggravates the overhead capacity overload problems that caused it to occur. Part or all of that free water in the reflux then ends up in the esterification reactor, where it adversely affects the reaction equilibrium and also consumes extra heat when it is vaporised again. This is typically indicated by a temporary bulge in the reactor pressure profile followed with some delay by a temporary dip in reaction temperature, deviating then from its optimal value. This has a negative impact on batch time, and the temperature fluctuations reduce the accuracy of any predictions regarding the batch time that is required for reaching the target conversions.

Alternatively, the alcohol may be recycled by allowing the vapor from the reaction vessel to be passed through a condenser and then the condensate passed to an overhead collection drum which allows the excess alcohol and the water to separate into two liquid phases; separating the excess alcohol from the water; recycling the excess alcohol through a heater and to a flash drum thereby producing a water-rich vapor, which is taken out overhead and preferentially combined with the vapors from the reaction vessel, and an excess alcohol-rich and water-lean liquid, which is recycled to the reaction vessel, optionally through an additional reflux drier. The water from the overhead separator may be recycled to the neutralisation and/or catalyst hydrolysis step. The vapors from the collection drum may be taken to a second condensor for condensation of water contained therein. Optionally the condensate from these vapors is recycled to the hydrolysis step.

We have found that, in particular when no reflux drying is performed but even when a reflux drier and/or flash step is provided, stopping the alcohol reflux to the reactor before the end of the run is reached, allows to drive the reaction faster to completion because absolutely no more water is returned to the reactor and its overhead system and at the same time reduces the amount of excess alcohol in the crude ester, such as down to 12-15% wt, thereby reducing the volume of crude ester to be further processed and the amount of alcohol that needs to be removed in the downstream finishing steps. We therefore prefer to stop the alcohol reflux at least 2 minutes, preferably at least 5 minutes, more preferably at least 7 minutes and even more preferably at least 10 minutes and even 15 minutes before the batch termination time. We have found that when the reflux is continued till the end of the batch and through a reflux drier, the water content of the crude ester at the end of the reactor run may still be as high as 50 ppm wt. When stopping the alcohol reflux about 12 minutes before the end of the batch, i.e. before the batch termination time, the water content of the final crude ester may be as low as only 20 ppm by weight, or may even be 10 ppm wt or below. We have found that the presence of water, even in these small amounts, may have a surprisingly large effect on the rate of the reaction at the end of run, and therefore on the completion of the reaction.

When the reflux to the reactor, or to the reflux drying step, is stopped, the alcohol coming from the overhead collection drum is routed to the recycle alcohol tank. When the batch is to be terminated, heat input to the reactor is stopped and the vacuum is broken, preferably by allowing nitrogen into the reactor system, more preferably into the reactor overhead system. This breaking of the vacuum is considered the moment of termination of the batch. As soon as the vacuum is broken, the reactor content may immediately be evacuated to a collection vessel in and from which it may be further processed. In case the next batch of product is of the same quality, the reactor is then ready for starting the new batch.

We prefer that esterification reactions be performed in the manner described in our copending U.S. patent application U.S. Ser. No. 60/906,797 (applicant's reference PM2004-063) wherein the temperature and pressure during at least the first stage of the esterification reaction are controlled to optimise the reaction rate and reduce reaction batch time. A particularly preferred reaction cycle for the production of esters and in particular plasticiser esters comprises the feed recipe adjustment of the present invention followed by the employment of the reaction cycle of our copending U.S. patent application U.S. Ser. No. 60/906,797 (applicant's reference PM2004-063) followed by the neutralisation technique of WO2006/125670 and the purification techniques of WO2005/021482.

Following esterification the crude ester is first passed into and through a neutralizing drum, where it is preferably contacted with an aqueous solution of sodium carbonate of a concentration less than the stoichiometric equivalent of the acidity of the crude ester. We prefer that the solution contains no more than 10% sodium carbonate and that it provides from 0.7 to 1.4 wt % water, based on the weight of the crude ester. We also prefer that a major portion of the ester has a residence time in the drum of at least 20 minutes. Following the neutralization, water is removed, preferably by flashing off, and the crude ester material is then filtered, preferably through a non metallic filter.

The following steps may be employed in ester purification after neutralisation: addition of adsorbents such as alumina, silica gel, activated carbon, clay and/or filter aid to the ester mixture; filtration of solids from the ester mixture containing the bulk of the excess alcohol used in the esterification process; removal of the excess alcohol by flashing and/or stripping; and removing any residual solids from the stripped ester by means of secondary filtration.

After the ester which has been neutralized has been filtered, it may be subject to further purification by stripping, and/or by a further filtration which may employ filter aids and absorbents such as is discussed in WO2005/021482. Where these techniques are used, materials that may be used as both filter aids and adsorbents include bleaching earth's, bentonites or activated clays, containing attapulgite or Fuller's Earth, montmorillonite, kaolinite and muskovite minerals. Examples of adsorbents that may be used are activated alumina, activated china clay, activated carbon, magnesium oxide, aluminium oxide and silicon oxide. These may be used either singly or in combination. The amount of the adsorbent used should be between 0.1 and 1% by weight based on the weight of the crude ester.

When this additional purification step is employed, we prefer to use from 0.01 to 5 wt % of the adsorbent or the combination of the adsorbent and the filter aid, based on the weight of the plasticiser ester to be purified. More preferably we use from 0.02 to 2 wt %, most preferably 0.03 to 1 wt %, and in particular 0.04 to 0.3 wt %. Although the filter aid or the activated carbon may be used alone, we prefer to use a mixture and that the mixture contains from 90 or 70 to 30 parts by weight of the filter aid and from 10 or 30 to 70 parts by weight of the adsorbent, more preferably the mixture contains 60 to 40 parts by weight of the filter aid and from 40 to 60 parts by weight of the absorbent. Our most preferred mixture contains from 45 to 55 parts of the adsorbent. For cost reasons, a lower content of adsorbent is preferred, but as the level of adsorbent is reduced, also its effect is reduced. We therefore prefer to use at least 30 parts by weight in the mixture. However, when the filter aid is particularly effective by itself, the active carbon may also be reduced to as low as 10%, 15% or 20% by weight of the mixture. These techniques are particularly useful to keep the level of light ends and odour components low in the final product. A low content of light ends and odour formers is also important when the product is to be used in a confined space such as a space capsule, an aeroplane or truck cabin, a car interior or a green house. When in the above technique a mixture is used, the filter aid and the adsorbent may be added separately to the plasticiser ester, although we prefer that they be added as a mixture, as this enables the use of a single injection position in the purification vessel.

The adsorbent and/or the filter aid are preferably added continuously to the plasticiser flowing through a stirred vessel which is optionally provided with baffles to enhance mixing. This addition may occur in a separate vessel located immediately upstream of the filter. The vessel is preferably the neutralization drum.

In preferred embodiments the process includes a flash step to flash off the free water phase between the neutralization drum and the filter. The water level is preferably reduced to no more than 500 ppm by weight. The flash step can also remove any or part of the unreacted alcohol which can then be recycled to the esterification reaction. In a further preferred embodiment an absorbent and/or a filter aid is added in the neutralization drum. The removal of the free water is important in the reduction in the build up of pressure drop in the filter as it improves the filterability of the solids to be filtered, in particular when sodium (bi-)carbonate is present. The filter cleaning becomes easier, and the filtered solids are easier to dispose of as a cake rather than as a slurry. Filtration with free water present also causes mono-ester and soda ash to remain dissolved, such that it has to be removed downstream by e.g. a washing step or a second (dry) filtration step. Flashing the water off before filtration causes the monoesters or their salts, and the sodium (bi-)carbonate to precipitate and to become filtrable. We have found that the water flash is preferably done in two stages. This improves the crystal growth, which helps the filtration. The second flash step may be performed under deep vacuum, such as at a pressure below 50 mm Hg absolute, preferably at around 10 mm Hg absolute, such that even lower water levels are achieved, crystal growth and size of the sodium and/or titanium solids is improved, and the formation of a titanium slime, which is difficult to filter, is avoided.

In a further preferred embodiment the neutralization vessel is a vertical drum provided with one or more baffles to form compartments and/or mechanical stirring to enhance mixing. The crude ester is preferably injected into the top of the vessel and the soda ash and water is preferably injected into the stream of crude ester shortly before it enters the vessel. The vessel is preferably at a temperature in the range of 100° C. to 140° C. and the pressure in the vessel should be sufficient to prevent the water vapourising. The amount of sodium carbonate that is used should be less than a stoichiometric amount in relation to the acidity of the crude ester and the preferred amount depends upon the speed of flow of the crude ester, the temperature in the neutralization drum and the residence time of the ester in the drum. However, it is important not to use more soda ash than is required for the neutralization, since this can lead to residual sodium in the ester and to the formation of haze in the purified ester.

The amount of water that should be added is from 0.7 to 1.4 wt % based on the weight of crude ester. The preferred amount of water depends on the nature of the ester. Relative to the total feed rate of crude ester to the hydrolysis drum and expressed in weight percent, the preferred and more preferred amounts of hydrolysis water are as stated in Table 1. The preferred and more preferred amounts of water depend also on the catalyst concentration used, and the numbers are given in Table 1 for different esters, and for two levels of tetra-isooctyl-titanate used as catalyst, which is expressed in % wt relative to the amount of phthalic anhydride reagent used in the esterification reaction. The percentage of hydrolysis water may also slightly be adjusted downward if throughput is reduced.

TABLE 1

| Ester produced | Catalyst Concentration | Preferred wt % Water | More preferred wt % Water |
| --- | --- | --- | --- |
| di-C7 phthalate | 0.016-0.017% wt | 1.0-1.5 | 1.2-1.4 |
| | 0.030-0.033% wt | 1.1-2.0 | 1.3-1.5 |
| di-C9 phthalate | 0.018-0.019% wt | 0.9-1.3 | 1.1-1.2 |
| | 0.034-0.037% wt | 1.1-1.5 | 1.2-1.3 |
| di-C10 phthalate | 0.018-0.019% wt | 0.9-1.3 | 1.0-1.1 |
| | 0.035-0.037% wt | 1.0-1.5 | 1.1-1.2 |
| di-C11 phthalate | 0.019-0.021% wt | 0.8-1.3 | 0.95-1.05 |
| | 0.037-0.039% wt | 0.9-1.5 | 1.05-1.15 |
| di-C13 phthalate | 0.018-0.021% wt | 0.8-1.3 | 0.95-1.1 |
| | 0.034-0.039% wt | 0.9-1.5 | 1.05-1.2 |

All catalyst concentrations in Table 1 are expressed as wt % titanium on phthalic anhydride charged into the reactor. The water is expressed as wt % on crude ester.

The process may alternatively be operated with higher amounts of water, in which case a separate water phase may be separated from the crude ester. Mono-esters and/or their salts may end up in this wash water, and particularly the salts may be difficult to remove from it. Their presence may be undesirable from an environmental or industrial hygiene point of view. We have found that an additional heat soaking step on this waste water is helpful in saponifying the mono-ester and/or hydrolyzing its salt, and allows for recovery of at least a part of the alcohol that is liberated from the hydrolysis. This may be done by heating the waste water, e.g. to 200-220° C., and under sufficient pressure to keep it liquid, such as 30-40 bar, and by holding it at that temperature for a certain time, such as 10-20 minutes. It may subsequently be cooled, e.g. to 90-120° C., and allowed to settle in a drum, optionally provided with baffles, for another given time, such as 2 to 3 hrs, again at a pressure above its vapor pressure. The organic phase may contain useful alcohols and esters, and may be recovered from this settling drum, and optionally be recycled, while the water phase will contain less organics and be easier to dispose of.

We have found that, by adjustment of the batch reaction recipe according to the present invention, it is possible to maintain high reactor productivity over longer periods of time despite the decreasing purity of the overall alcohol feed, and it is possible to operate with accurately predictable reaction batch times, which allows reactor productivity to be even higher. Accordingly by analysis of composition of the fresh alcohol and comparing the predicted and actual alcohol content in the recycle alcohol, the feeds may be combined in the optimum ratio for reactor productivity.

Some esterification processes may suffer so much byproduct losses at different locations in the process, that the level of impurities in the recycle alcohol never reaches levels that become economically disadvantaged. This is more likely to occur when the feedstocks, in particular the alcohol feedstock, are of extra high purity. Also the use of mild catalysts, such as titanates may help to create such situations.

In many cases however, the recycle alcohol eventually becomes so impure that it must be discarded. This may more likely occur when acidic catalysts are used, like sulphuric acid or toluene sulphonic acid, which may cause the formation and buildup of colour precursors in the recycle alcohol. Discarding the recycle alcohol at a certain stage may then be required to maintain the product quality of the plasticiser ester, in particular regarding colour. Use of the techniques of the present invention have been found to reduce the amount of alcohol that is discarded.

Several methods exist to discard such recycle alcohol containing high levels of impurities. The most common method is to simply discard the recycle alcohol as such. However the 70-90% wt of useful alcohol discarded with it is still of value. An improvement is to produce a special ester batch with a higher than usual recycle alcohol content, before discarding the remaining recycle alcohol. The special batch may then have a very high color and may be sold separately as off-spec product into an application that is not colour sensitive. The purity of the discarded alcohol is often 70-90% alcohol content.

An improved strategy is to produce, in a first stage, a long series, e.g. of 64 batches, all with fresh alcohol only, and recovering the excess alcohol from all these batches as recycle alcohol. In a second stage, a shorter series, e.g. of 8 batches is prepared using all or a significant part of the recycle alcohol of the first series, typically resulting in a product with an increased color. In a third stage, the recycle alcohol left over from the second stage is then used to prepare one batch with a very high off-spec color, followed by the purging/discard of the recovered excess alcohol from this batch. The ester products of the first two stages, or if possible even of all three stages, is blended. In the latter case, the overall color of the blend may still be only 13-15 Pt/Co versus 20-25 Pt/Co when the recycle alcohol is continuously reused.

The buildup of inerts in the recycle alcohol typically requires a continuous monitoring of the alcohol content of the recycled alcohol. At a constant true molar excess of alcohol, the total amount of inerts present during the esterification reaction increases accordingly. This results in a lower ester production per batch and an increasing use of energy to handle the inerts in the process. At a given point the purging of the inerts and the recycle alcohol becomes necessary, when the value of the lost alcohol is lower than the lost production and the additional energy costs if one would continue. The purity of the discarded alcohol is then typically 50-75% alcohol content.

Most of the conventional discard methods have the disadvantage that a lot of useful and valuable alcohol is discarded. The fuel value of the discarded recycle alcohol is significantly below its value as a chemical raw material. Rework through a distillation unit followed by optionally hydrogenation has been attempted, but only with occasional success. This only works well if the inert components can be easily separated from the alcohol. However, most of the time the inerts present are those from the alcohol feed, which are difficult to separate by conventional separation techniques as they otherwise would not have been present in the alcohol feed in the first place. In such a case most of the inerts are continuously recycled between the esterification facility and the alcohol distillation unit. This is not very economical due to the increased cost of energy for the processing steps.

An improved recovery method is to apply chemical separation rather than physical separation. This method is explained here for the batch production of di-isononyl phthalate and di-isodecyl phthalate, but may be readily adapted to production processes of other esters in which an excess of alcohol is used in the reaction recipe.

We have found it useful to apply this method when the alcohol content of the recycle alcohol has become reduced to at most 90% wt, preferably at most 85% wt, more preferably at most 80% wt, and even more preferably at most 76% wt. We prefer to apply the method when the alcohol content of the recycle alcohol is at least 65% wt, preferably at least 70% wt, more preferably at least 74% wt, in particular for C9 alcohol, and even more preferably at least 76% wt, in particular for C10 alcohol.

Recycle alcohol of such quality, and phthalic anhydride, are added to an esterification batch reactor, in a ratio such that the true stoichiometric alcohol excess is in the range of 5-30%, preferably 10-25%, more preferably 15-20% and most preferably about 15%. In a first step, a reaction procedure such as explained before is applied until a target conversion is reached, calculated on the amount of phthalic anhydride present. We prefer to use a catalyst in this first esterification step, and we prefer to use a titanium catalyst. During this first esterification step, preferably only water is removed from the reactor overhead system, and organics are refluxed to the reactor. We have found it of interest to minimise the amount of acid that remains at the end of this reaction step. We therefore prefer to run the reaction until a conversion of at least 90%, preferably at least 95%, more preferably at least 97%, even more preferably at least 98.5%, and most preferably about 98.7% is reached, calculated on the phthalic anhydride.

In a second step, the excess alcohol and the inerts, primarily the monomeric but also some of the intermediate and dimeric impurities, are boiled off from the reactor, as in a batch distillation operation, and collected into the reactor overhead condensor system. Preferably no reflux is applied to the reactor during this distillation step. It has been found that the remaining intermediate ester, due to incomplete acid conversion, does not necessarily decompose during the batch distillation. We have also found that this distillation operation may be performed under conditions such that no loss of catalyst activity is suffered for the subsequent reaction stage. Preferably when the distillate flow rate slows down, the batch distillation is stopped. A major part of the organic material that had been collected in the reactor overhead system during the first step and during the distillation, is then preferably removed from the overhead system into the separate distillate tank, preferably for being discarded. The alcohol content of the resulting distillate or material for discard may then be as low as 25-30%. It is assumed that no more free alcohol is present in the mixture left over in the reaction vessel after the distillation.

In a third stage, fresh alcohol is added to the mixture in the esterification reactor, and we prefer to add fresh alcohol in an amount such that the preferred molar excess ratios for the particular product grade are reached. In addition, we prefer to add an amount of fresh alcohol sufficient to fill up the volume of organics required to operate the reactor overhead and reflux system. If desired, another amount of catalyst may be introduced at this stage, or during the second esterification step. Subsequently, the reaction is restarted and a second esterification step is continued to reach the standard high target of at least 99%, preferably at least 99.5%, and more preferably at least 99.9% conversion, based on acid. With this approach, the lost alcohol content in the discarded alcohol is significantly reduced from 75% down to 25-30% wt without needing repeated recycling and without producing highly colored ester product. We have also found that, when experience is gained, the steps in this method may be operated on preset time intervals, rather than on the conversions reached, so that the method is suitable for being automated, and any sampling and analytical measurements become only necessary for verification purposes.

Further productivity benefits may be achieved in esterification processes that produce more than one ester product, and which on a regular basis have to switch from one product to another. The conventional method is to shut down and empty the unit and clean the equipment by e.g. a water wash. This introduces a significant amount of down time, and possibly generates substantial volumes of waste water that needs to be disposed of. An alternative is a dry changeover, thus eliminating the use of water, but which because of grade cross-contamination typically produces a certain volume of mixed grade product material, which is generally not compliant with any of the individual product grade specifications and therefore may need to be downgraded to a lower sensitivity end-use or be reworked.

Our preferred method is to apply a "flying grade-switch" procedure. The objective of this flying grade-switch is to minimize the production loss and the grade cross-contamination, while switching from one alcohol feed grade to another. The flying grade-switch is executed by maximizing the feed rate to the finishing unit, while having at the same time a minimum liquid holdup. As a preparation for a flying grade-switch, exemplified here in a batch reactor unit combined with a continuous finishing unit, all drum levels are gradually reduced to the minimum level required to keep the esterification unit pumps and mixers running. This also allows for a continued operation of the solids addition systems. Furthermore, all precoat filters are being switched just before the completion of the first batch of the new grade. The precoat drum, where the filter precoat material is mixed with liquid before transfer to the filter system, is being emptied into the filtration feed drum prior to the grade switch.

The alcohol feed line and the alcohol feed drum are being emptied into the last reactor batch of the old grade. In tankage, the feed alcohol and recycle alcohol tanks are then switched over to the new grade, and the reactor feed drum is filled with the new alcohol grade. The new grade recipe is loaded into the reactor process control system. The reactor section is now ready for the production of the first batch of the new grade.

After dumping the last batch of crude ester of the old grade, the feed drum of the continuous finishing unit is emptied to reach about 10% drum level just before dumping the first batch of the new grade into that drum. At this time, the adsorbent and/or filter aid solids addition to the feed drum of the secondary filtration unit, which is typically located downstream of the excess alcohol stripper tower, is preferably also already stopped, and this preferably when the drum content has first been reduced to its minimum level. After dumping the first batch of the new grade into the finishing feed drum, the hydrolysis water ratios are typically adjusted to the requirements of the new grade.

After feeding 45% of the total volume of new crude ester, required for flushing out the old grade from the continuous finishing section, the liquid circulation flows over the secondary filtration unit and its dosing system are also stopped, while the stripper feed preheater temperature is adjusted to the new conditions. When reaching 90% of the required flushing volume, the operator starts checking the density of the plasticizer rundown product. At 100% of the flushing volume, the recycle alcohol rundown from the stripper is switched from the old grade tank to the new grade tank.

After measuring the target plasticizer density for the new grade, the rundown of the unit is switched from the old grade to the new grade tank. The circulation flows over the secondary filtration unit and its dosing system are restarted. The filtration drum levels are being reestablished followed by restarting the mixers and the adsorbent and/or filter aid dosing. All other drum levels are now being returned to their target values.

We have found that the flying grade-switch procedure may be more difficult to apply in a process that produces a wide variety of product qualities. We have found that it is particularly suitable for a process that produces esters from only a limited number, preferably only one type, of acid or anhydride starting material, such as a process that produces primarily phthalate esters. It is even more suitable for a process that processes only a limited number of different alcohol starting materials. If these alcohol starting materials differ in carbon number, the flying grade switch is particularly suitable if there are only small differences between the average carbon numbers of the individual alcohol qualities. We prefer to schedule production in a multiproduct phthalate ester plant such that consecutive campaigns of phthalate product qualities do not differ more than about 3 carbon atoms, preferably not more than about 2 carbon atoms, and more preferably not more than about 1 carbon atoms with respect to the average carbon number of their alcohol starting materials. Such production sequences allow to apply the advantageous flying grade switch procedure while minimizing the degree of product cross-contamination, that is inevitable in such procedure, and any possible effect thereof on product performance. We also prefer to run the campaigns of a single product quality as long as possible, i.e. with as many as possible consecutive batches, as allowed by feed availability, product storage capacity, and product demand. This further reduces the amount of product cross-contamination between two consecutive product campaigns.

The invention is further illustrated by the following examples. In these examples, an estimated recycle alcohol purity is calculated from the purity analysis of the fresh alcohol feed by applying a mass balance model, which is based on assuming that the alcohol impurities concentrate from the fresh alcohol into the recycle alcohol by a typical factor derived empirically, and on the known inventory of the recycle alcohol in the facilities.

Example 1

A stirred tank reactor was filled with (at 150° C.) 26.2 m3 of a preheated $C_{10}$ alcohol derived from a branched nonene containing 10 ppm Annulex BX inhibitor, 6.2 m3 recycle $C_{10}$ alcohol with an actual and calculated purity of 80% by weight and 9.9 tons of phthalic anhydride. This corresponds to a molar excess of 22.5% of alcohol over acid in the reaction mixture. The reactor contents were further heated with high pressure steam and, when the temperature reached 180° C., 42 liters of tetra-iso-octyl titanate were injected into the reaction mixture, followed by continued heating to 220° C., the target reaction temperature. At 215° C. the pressure in the reactor was gradually started to be reduced from atmospheric pressure (100 kPa) to 30 kPa with the objective to ensure continuous alcohol reflux at a constant reaction temperature of 220° C. After 119 minutes from the start of filling the reactor, a monoester conversion of 99.96% was obtained. The total cycle time from the start of the batch to a fully emptied reactor was 131 minutes.

Comparative Example 2

In this example the importance of correctly calculating the recycle alcohol purity is illustrated. Errors may occur in the alcohol feed purity analysis, and deviations from typical may occur in the empirical factor and/or in the recycle alcohol inventory, each possibly causing an incorrect estimate of the recycle alcohol purity. The need for corrective actions are established by regularly analyzing the recycle alcohol and adjusting the alcohol purity in the calculations for the analytical result.

A stirred tank reactor was filled with (at 150° C.) 26.2 m3 of a preheated $C_{10}$ alcohol derived from a branched nonene containing 10 ppm Annulex BX inhibitor, 6.2 m3 recycle $C_{10}$ alcohol with a calculated and estimated purity of 80% by weight, but which in reality only contained 75% purity and 9.9 tons of phthalic anhydride. This corresponds to a molar excess of only 21.5% of alcohol over acid in the reaction mixture, rather than the estimated 22.5% excess. The reactor contents were heated with high pressure steam and, when the temperature reached 180° C., 42 liters of tetra-iso-octyl titanate were injected into the reaction mixture followed by continued heating to 220° C., the target reaction temperature. At 215° C., the pressure in the reactor was gradually started to be reduced from atmospheric pressure (100 kPa) to 30 kPa with the objective to ensure continuous alcohol reflux at a constant reaction temperature of 220° C. After 122 minutes from the start of filling the reactor a monoester conversion of 99.96% was obtained. The total cycle time from the start of the batch to a fully emptied reactor was 134 minutes.

Comparative Example 3

In this example the recycle alcohol purity is not monitored, but assumed to be constant for each of the batches in a campaign. The actual recycle alcohol purity drops without being noticed and causes excessive batch times by the reduced excess of alcohol and the boiling up of the non-alcohol components.

A stirred tank reactor was filled with (at 150° C.) 26.2 m3 of a preheated $C_{10}$ alcohol derived from a branched nonene containing 10 ppm Annulex BX inhibitor, 6.2 m3 recycle $C_{10}$ alcohol with an assumed purity of 80% by weight, but in reality only 50% purity and 9.9 tons of phthalic anhydride. This corresponds to a molar excess of only 16.5% of alcohol over acid in the reaction mixture, rather than the assumed 22.5% excess. The reactor contents were heated with high pressure steam and, when the temperature reached 180° C., 42 liters of tetra-iso-octyl titanate were injected into the reaction mixture followed by continued heating to 220° C., the target reaction temperature. At 215° C., the pressure in the reactor was gradually started to be reduced from atmospheric pressure (100 kPa) to 30 kPa with the objective to ensure continuous alcohol reflux at a constant reaction temperature of 220° C. After 155 minutes from the start of filling the reactor a monoester conversion of 99.96% was obtained. The total cycle time from the start of the batch to a fully emptied reactor was 167 minutes.

These examples show that when the amount of alcohol recycled and the amount of fresh alcohol are not adjusted to take into account the varying amounts of impurities in the recycle alcohol throughout a sequence of reactor runs, the esterification runs may be performed at non-optimal reaction conditions, in particular at alcohol molar excess conditions that are below optimum and below estimates, at which the reaction batch times become longer and unpredictable. Under such circumstances, conversion monitoring by analysis may become necessary to assure a desired reaction conversion is reached, and further delays in batch times may be introduced because of that.

Having now fully described this invention, it will be appreciated by those skilled in the art that the invention can be performed within a wide range of parameters within what is claimed, without departing from the spirit and scope of the invention.

The invention claimed is:

1. A process for producing an ester comprising:
   (i) esterifying an acid or anhydride with an excess of an alcohol to produce a crude ester in a first esterification reaction,
   (ii) recovering excess recycle alcohol from the crude ester formed by the esterification,
   (iii) recycling said recovered excess recycle alcohol of the first esterification reaction together with fresh alcohol, characterised by controlling the ratio of the amount of recycle alcohol of step (ii) and the amount of fresh alcohol in dependence on the level of the impurities in the recycle alcohol of step (ii), to control the true molar excess of the alcohol,
   (iv) reacting a stoichiometric excess of said recycle alcohol, having an alcohol content of at most 90% wt, with acid or anhydride in a separate, second esterification reaction to a conversion of at least 90%, calculated on the acid or anhydride,
   (v) boiling off excess alcohol and inerts from the second esterification reaction mixture in a distillation step,
   (vi) adding fresh alcohol to the reaction mixture after the distillation step, and
   (vii) reacting the mixture formed in step (vi) to a conversion of at least 99%, calculated on the acid or anhydride.

2. The process according to claim 1, for the production of a phthalate di-ester and wherein the acid or anhydride is phthalic acid or anhydride, which comprises providing a true (excluding impurities) molar stoichiometric excess of alcohol relative to phthalic acid or anhydride that is in the range of from 22% to 32%.

3. The process according to claim 1 which further comprises removing oxygen from the fresh alcohol before the fresh alcohol is mixed with the recycle alcohol.

4. The process according to claim 1 wherein the catalyst that is used is a titanium catalyst.

5. The process according to claim 1 for the production of a phthalate di-ester, further comprising hydrogenating the phthalate di-ester to produce the corresponding di-alkyl cyclohexanoate di-ester.

6. The process according to claim 1 wherein the ester conversion of the first esterification reaction is at least 95%.

7. The process according to claim 1 wherein the ester conversion of the first esterification reaction is at least 97%.

8. The process according to claim 1 wherein the ester conversion of the first esterification reaction is at least 99%.

* * * * *